(12) United States Patent
Fujihara et al.

(10) Patent No.: US 7,951,533 B2
(45) Date of Patent: *May 31, 2011

(54) STRUCTURE DETERMINING METHOD OF FUNCTIONAL SUBSTANCE HAVING AFFINITY TO BIOMOLECULE OR CHEMICAL, AND METHOD FOR PRODUCING FUNCTIONAL SUBSTANCE

(75) Inventors: Tsuyoshi Fujihara, Kawasaki (JP); Shozo Fujita, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/261,750

(22) Filed: Oct. 31, 2005

(65) Prior Publication Data

US 2006/0183135 A1 Aug. 17, 2006

(30) Foreign Application Priority Data

Feb. 14, 2005 (JP) ................. 2005-035875

(51) Int. Cl.
*C12Q 1/68* (2006.01)
*C12P 19/34* (2006.01)
*C07H 21/00* (2006.01)
*C07H 21/02* (2006.01)
*C07H 19/04* (2006.01)

(52) U.S. Cl. ......... 435/6; 536/23.1; 536/25.3; 536/26.6; 435/91.1

(58) Field of Classification Search .................. None
See application file for complete search history.

(56) References Cited

U.S. PATENT DOCUMENTS

| | | | |
|---|---|---|---|
| 5,763,175 A * | 6/1998 | Brenner ........................ 435/6 |
| 7,517,646 B2 * | 4/2009 | Fujihara et al. ............... 435/6 |
| 2003/0235852 A1 * | 12/2003 | Roberts et al. ............... 435/6 |
| 2005/0130195 A1 * | 6/2005 | Fujihara et al. ............... 435/6 |

FOREIGN PATENT DOCUMENTS

| | | | |
|---|---|---|---|
| EP | 1 489 171 A1 * | 12/2004 |
| JP | 10-508304 | 8/1998 |
| JP | 2002-291491 | 10/2002 |
| JP | 2004-337022 | 12/2004 |
| WO | WO 03/078623 | * | 9/2003 |
| WO | WO 03/078623 A1 * | 9/2003 |
| WO | WO 2005/003304 A2 | 1/2005 |

OTHER PUBLICATIONS

Englisch et al., Chemically Modified Oligonucleotides as Probes and Inhibitors, Angew. Chem. Int. Ed. Engl. 30 (1991) 613-629.*

Anna V. Kachalova et al., "Synthesis of Modified Nucleotide Building Blocks Containing Electrophilic Groups in the 2'-Position", *Nucleosides, Nucleotides & Nucleic Acids*, vol. 19, No. 10-12, 2000, p. 1693-1707.

* cited by examiner

*Primary Examiner* — Mark Staples
(74) *Attorney, Agent, or Firm* — Kratz, Quintos & Hanson, LLP

(57) ABSTRACT

Novel technologies are provided to determine the structure of and produce a functional substance that has a high affinity to a target. Candidates for a substance having an affinity to a target (functional substance) are synthesized; a functional substance that has an affinity to the target is selected from among the functional substance candidates; a specific substituent group is eliminated from the selected functional substance; the functional substance from which the specific substituent group has been eliminated is amplified; the structure of the amplified functional substance is determined; and the functional substance is produced, based on the structure.

10 Claims, 9 Drawing Sheets dA Amidite ; Base =  ···(41)

dG Amidite ; Base =

···(42)

dC Amidite ; Base =  ...(43)

dT  Amidite ; Base =  ...(44)

dG' Amidite ; Base =

···(45)

dT' Amidite ; Base =

···(46)

dT'' Amidite ; Base =

5- Propagylamino dU dT''' Amidite ; Base = dT""

dT"""

STRUCTURE DETERMINING METHOD OF FUNCTIONAL SUBSTANCE HAVING AFFINITY TO BIOMOLECULE OR CHEMICAL, AND METHOD FOR PRODUCING FUNCTIONAL SUBSTANCE

CROSS-REFERENCE TO RELATED APPLICATIONS

This application is based upon and claims the benefit of priority from the prior Japanese Patent Application No. 2005-035875, filed on Feb. 14, 2005, the entire contents of which are incorporated herein by reference.

BACKGROUND OF THE INVENTION

1. Field of the Invention

The present invention relates to a functional substance (in the present invention, a substance that has an affinity to a target is called a functional substance) that shows a high affinity and/or high recognition specificity to various targets, is applicable to medicines, drug delivery, biosensors, control of gene expression level, overcoming of diseases due to gene defects, elucidation of functions of proteins translated by genes, development of reactive catalysts, etc., and is particularly favorable for analyzing and/or screening of proteins, as well as a method for producing the functional substance efficiently.

2. Description of the Related Art

With the development of bioscience, the focus of interest of researchers and scientists is shifting to analysis of proteins which are products by genes. The analysis of proteins is often performed through analysis of substances having affinities to individual proteins to be inspected.

Therefore, it is no exaggeration to say that the analysis of a protein is made possible only when there is a substance that has an affinity to the protein. Proteins to be analyzed are present in cells in a great variety and most of their amino-acid sequences, structures, etc. are quite unknown. Various substances are thus necessary in order to analyze proteins.

However, by now, efficient methods to produce or obtain such substances for analyzing proteins have not been sufficiently established. As the most general method for obtaining substances having affinities to specific proteins, methods to select affinity antibodies using animal immune systems are known. However, since these methods use animals, they require a large amount of proteins and numerous processing steps, and are accordingly costly. In addition, the affinity antibodies thus selected and obtained cannot be amplified (that is, reproduced). Also, there is a problem that only those which have an affinity to the same target are selected. Thus, it is extremely difficult to select individual affinity antibodies that have affinities to a great variety of proteins existing in cells, and obtain a sufficient amount of them.

Regarding the synthesis of proteins having gene information, there was a study in which puromycin was introduced into the 3'-terminal of an mRNA (Japanese Unexamined Patent Application Publication No. 2002-291491, claims, for example). This utilizes the property of puromycin being liable to be mistaken by a translation system as an amino acid and incorporated into a protein. However, the incorporation efficiency of puromycin has been rather low, and there have been only some reports in which functional substances have been selected from a library having random three amino acid residues.

On the other hand, as a method for identifying proteins using antibodies, the immunosensor amperometric method has been developed, for example. With this method, a tiny amount of proteins as small as about 2 ng/L can be measured. However, there are problems that almost all antibodies are not bound with proteins in a protein solution having such a low concentration, and that many non-specific reactions would occur in a solution (serum, for example) containing a lot of foreign substances, lowering the measurement accuracy.

In addition, although various proposals have been made including a supermolecule assembly that can coat viruses, etc. (Japanese Unexamined Patent Application Publication No. H10-508304, claims, for example), they have problems that the structures are complicated, and it is not possible to efficiently produce substances having affinities to many targets that are higher than those of antibodies.

There is a manufacturing method in which a mixture is synthesized that has numerous candidates for a substance having an affinity to a target, each in an extremely tiny amount; a substance that has an affinity to the target is selected from the substance candidates; the selected substance is then amplified in one way or another; the structure is analyzed using the amplified substance; and the substance for the purpose is selectively synthesized, based on the analyzed structure (Japanese Unexamined Patent Application Publication No. 2004-337022, paragraph number [0040], for example).

When a case is taken for an example in which the target is a protein, and a substance having a function such as described above is a nucleotide sequence, a mixture is synthesized that has numerous nucleotide sequences as candidates; a nucleotide sequence that has an affinity to a target protein is selected from among the numerous nucleotide sequences; it is amplified; the base sequence of this amplified nucleotide sequence is then determined; and the nucleotide sequence having an affinity to the target protein is produced, based on the determined sequence (that is, the determined structure).

In this way, it is possible to determine a functional substance for the purpose from among a tiny amount of functional substance candidates, and to realize its production. Accordingly, it is possible to quickly develop a sufficient amount of a novel functional substance.

If a sufficient amount of a functional substance is available, analysis of the structure of a target (sequence structure of a protein, for example), screening thereof, etc. can be developed by analyzing the structure, so that the result is applicable to medicines, drug delivery, biosensors, control of gene expression level, overcoming of diseases due to gene defects, elucidation of functions of proteins translated by genes, development of reactive catalysts, etc.

However, there is a problem that some of the selected functional substances cannot be amplified, and therefore, a sufficient amount of functional substances is not available. For example, while a PCR (Polymerase Chain Reaction) is often utilized in this amplification, some of the selected functional substances hinder the amplification by a PCR. When a selected functional substance has a strong positive charge or in a similar occasion, such hindrance occurs. If the amplification is hindered, it is not possible to determine the structure or produce the functional substance which are to be carried out after the amplification.

One of the causes is, for example, substituent groups introduced for the purpose of improving the affinity of functional substances to proteins that hinder the amplification reaction by a PCR or the like.

SUMMARY OF THE INVENTION

One object of the present invention is to solve such a problem, and to develop novel technologies that make it possible to determine the structure of and produce a functional substance that has a high affinity to a target. Other objects and advantages of the invention will become apparent from the following explanations.

According to one aspect of the present invention, provided is a method for determining the structure of a functional substance comprising: synthesizing candidates for a substance having an affinity to a target (functional substance); selecting a functional substance that has an affinity to the target from among the functional substance candidates; eliminating a specific substituent group from the selected functional substance; amplifying the functional substance from which the specific substituent group has been eliminated; and determining the structure of the amplified functional substance.

According to another aspect of the present invention, provided is a method for producing a functional substance comprising: synthesizing candidates for a substance having an affinity to a target (functional substance); selecting a functional substance that has an affinity to the target from among the functional substance candidates; eliminating a specific substituent group from the selected functional substance; amplifying the functional substance from which the specific substituent group has been eliminated; determining the structure of the amplified functional substance; and producing the functional substance, based on the structure.

By these aspects of the present invention, novel technologies that make it possible to determine the structure of and produce a functional substance that has a high affinity to a target are provided.

In both aspects, preferable are that the specific substituent group comprises at least one group selected from the class consisting of natural or non-natural amino acid groups, metal complex groups, fluorescent pigment groups, oxidation/reduction pigment groups, groups which can be spin-labeled, alkyl groups with a carbon number from 1 to 10, as well as groups represented by formulae (1) to (10) each group of which may have a substituent group

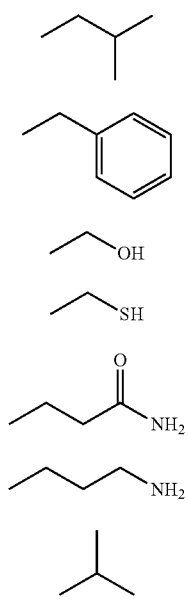

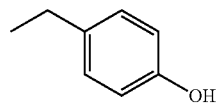

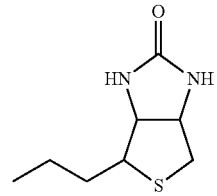

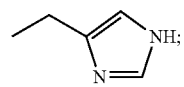

that the specific substituent group is eliminated from the functional substance, by scission of a cis-diol by means of periodic acid oxidation, by scission of a silyl group by means of a fluorine ion, by scission by means of an acid and alkali, by scission by means of an enzymatic reaction, or by scission by means of an optical reaction; that the functional substance comprises a modified nucleotide sequence; that the functional substance is a modified DNA sequence or a modified RNA sequence; and that the target is at least one substance selected from the group consisting of proteins, lipoproteins, glycoproteins, polypeptides, lipids, polysaccharides, lipopolysaccharides, nucleic acids, environmental hormones, drugs, composite materials thereof, and materials obtained by decomposing these materials.

By the present invention, novel technologies that make it possible to determine the structure of and produce a functional substance that has a high affinity to a target are provided.

DESCRIPTION OF THE PREFERRED EMBODIMENTS

Figure 1:
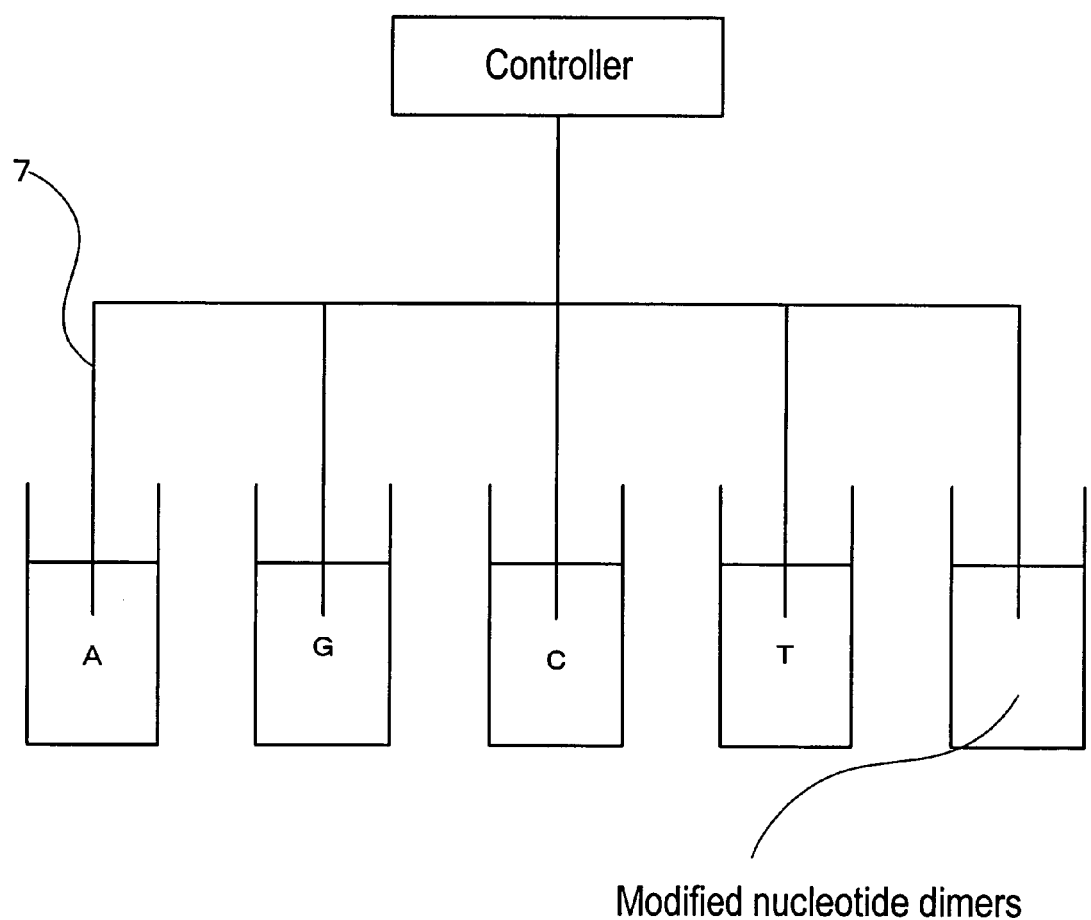
FIG. 1 is a schematic view of a DNA synthesizer.

Embodiments according to the present invention will be described below with reference to the following views, examples, etc. It is to be understood that these views, examples, etc., plus the explanation below are for the purpose of illustrating the present invention, and do not limit the scope of the present invention. It goes without saying that other embodiments should also be included in the category of the present invention as long as they conform to the gist of the present invention.

By a method for determining the structure of a functional substance according to the present invention, candidates for a functional substance is synthesized; a functional substance that has an affinity to the target is selected from among the functional substance candidates; a specific substituent group is eliminated from the selected functional substance; the functional substance from which the specific substituent group has been eliminated, is amplified; and the structure of the amplified functional substance is determined.

Furthermore, by a method for producing a functional substance according to the present invention, the functional substance is produced, based on the structure of the functional substance thus obtained.

(Target)

There is no particular limitation to the target according to the present invention, and any material can be appropriately chosen, depending on purposes. Proteins, lipoproteins, glycoproteins, polypeptides, lipids, polysaccharides, lipopolysaccharides, nucleic acids, environmental hormones, drugs, composite materials thereof, etc., are examples.

They may be used singly, or two or more of them may be used together. Among them, plasma proteins, tumor markers, apoproteins, viruses, autoantibodies, clotting/fibrinolytic factors, hormones, drugs in the blood, HLA antigens, environmental hormones, nucleic acids, etc., are favorable examples.

As the above-described plasma proteins, immunoglobulins (IgG, IgA, IgM, IgD, IgE), complement components (C3, C4, C5, C1q), CRP, $\alpha$1-antitrypsins, 1-microglobulins, $\beta$2-microglobulins, haptoglobins, transferrins, ceruloplasmins, ferritins, etc. are enumerated, for example.

As the above-described tumor markers, $\alpha$-fetoproteins (AFP), carcinoembryonic antigens (CEA), CA19-9, CA125, CA15-3, SCC antigens, prostatic acid phosphatases (PAP), PIVKA-II, $\gamma$-seminoproteins, TPA, elastase I, nerve-specific enolase (NSE), immunosuppressive acid proteins (IAP), etc., are enumerated, for example.

As the above-described apoproteins, Apo AI, Apo AII, Apo B, Apo CII, Apo CIII, Apo E, etc., are enumerated, for example.

As the above-described viruses, hepatitis B virus (HBV), hepatitis C virus (HBC), HTLV-I, HIV, etc., are enumerated, for example. As the infectious agents other than viruses, ASO, toxoplasmas, mycoplasmas, STD, etc., are enumerated. These disease germs as well as proteins produced therefrom are also enumerated as targets.

As the above-described autoantibodies, anti-microsome antibodies, anti-thyroglobulin antibodies, antinuclear antibodies, rheumatism factors, antimitochondria antibodies, myelin antibodies, etc., are enumerated, for example.

As the above-described clotting/fibrinolytic factors, fibrinogens, fibrin degradation products (FDP), plasminogens, $\alpha$2-plasmin inhibitors, antithrombin III, $\beta$-thromboglobulins, Factor VIII, Protein C, Protein S, etc., are enumerated, for example.

As the above-described hormones, hypophyseal hormones (LH, FSH, GH, ACTH, TSH, prolactins), thyroid hormones ($T_3$, $T_4$, thyroglobulins), calcitonins, parathormones (PTH), adenocorticotropic hormones (aldosterone, cortisol), gonadal hormones (hCG, estrogen, testosterone, hPL), pancreatic/gastrointestinal hormones (insulin, C-peptide, glucagon, gastrin), other hormones (renin, angiotensin I, II, enkephalin, erythropoietin), etc., are enumerated, for example.

Environmental hormones are environmental endocrine disturbing chemicals that are widely present in the surroundings, and taken into a body during various daily activities of natural life forms, influencing on various internal secretion-associated physiological phenomena, including reproduction, genesis, behavior, etc. As the above-described environmental hormones, nonylphenol, octylphenol, bisphenol A, butyl benzyl phthalate, tributyl tin, PCB, poly(dibenzodioxin chloride), poly(dibenzofuran chloride), dioxins, DDT, DDE, DDD, endosulfane, methoxychlor, heptachlor, toxaphene, dieldrin, lindane, diethyl stilbestrol (DES), ethinyl estradiol (an ingredient of a contraceptive pill), coumestrol, formonetin, genistein, etc., are enumerated, for example.

As the above-described drugs in the blood, antiepileptic drugs such as carbamazepine, primidone and valproic acid, drugs for circulatory diseases such as digoxin, chinidine, digitoxin, theophylline, antibiotics such as gentamicin, kanamycin, streptomycin, etc., are enumerated, for example.

As the above-described nucleic acids, cancer-associated genes, hereditary disease-associated genes, virus genes—bacterial genes, polymorphic genes that are referred to as risk factors of diseases, etc., are enumerated.

As the cancer-associated genes, K-ras genes, N-ras genes, p53 genes, BRCA1 genes, BRCA2 gene, src genes, ros genes, APC genes, etc., are enumerated, for example.

As the hereditary disease-associated genes, genes associated with various inborn errors in metabolism such as phenylketonuria, alcaptonuria, cystinuria, Huntington's chorea, Down's syndrome, Duchenne muscular dystrophy, hemophilia, etc., are enumerated, for example.

As the viruses—bacteria, hepatitis C virus, hepatitis B virus, influenza viruses, measles viruses, HIV viruses, mycoplasmas, rickettsias, streptococcuses, salmonellas, etc., are enumerated, for example.

As the polymorphic genes, genes with base sequences that are different from one another according to individuals, and are not necessarily directly associated with the causes of diseases, such as PS1 (presenilin 1) gene, PS2 (presenilin 2) gene, APP ($\beta$-amyloid precursor protein) gene, lipoprotein genes, genes associated with HLA (Human Leukocyte Antigen) and blood types, genes that are believed to be associated with crises of high blood pressure, diabetes, etc., are enumerated.

These targets are often contained in specific analytes. Thus, the targets according to the present invention may be used as analytes containing foreign substances. As such analytes, disease germs such as bacteria and viruses; blood, saliva, tissue fragments, etc. separated from a body; and excretory substances such as feces and urine are enumerated, for example. Furthermore, when a prenatal diagnosis is carried out, cells of a baby in the womb, part of egg cells undergoing division in test tube, etc. may be used. As a preliminary treatment, these analytes may be subjected to concentration directly, or, if necessary, by centrifugal separation or the like to form deposit, followed by cell destruction processing, for example, by treatment with an enzyme, thermal treatment, surfactant treatment, ultrasonic wave treatment, combination thereof, etc.

(Functional Substance)

A functional substance according to the present invention is a substance having an affinity to a target. A functional substance to be amplified is such a material which can be amplified if a certain substituent group contained in the substance is eliminated from the substance by one way or another. A functional substance to be produced by the present invention means such a functional substance to be amplified or its decomposed substance, or a substance comprising such a functional substance to be amplified or its decomposed substance.

Any substances may be accepted as such functional substances according to the present invention, as long as these conditions are satisfied. Those comprising a nucleotide bonding are preferable, since the amplification is easy. To be more specific, substances comprising modified nucleotide sequences (nucleotide sequences having modifying groups), modified DNA sequences or modified RNA sequences for example, may be enumerated. Either of the modifying groups in this case corresponds to the specific substituent group according to the present invention. There is no particular limitation to the number of bonds of the nucleotide sequences, and it may be appropriately chosen, depending on purposes. For example, 10-mers to 100-mers are preferable, and 10-mers to 50-mers are more preferable. It is to be noted that a nucleotide according to the present invention may be either a deoxyribonucleotide or a ribonucleotide.

There is no particular limitation to the affinity to a target, and any of biological adsorption, physical adsorption, electric attraction, chemical adsorption and chemical bonding may be applied. Those with a small dissociation constant (Kd) is preferable in terms of ease of selection. For example, those with a Kd of not more than $10^{-9}$ are preferable.

A functional substance according to the present that has an affinity to a target, is preferably one that has a specific affinity such as one indicating an affinity only to one specific target, or one indicating a specific affinity to targets having a specific structure (one indicating an affinity only to proteins that have a specific base sequence, or one indicating an affinity only to proteins that have a specific spatial configuration, for example).

(Specific Substituent Group)

Various substituent groups are introduced into the functional substance owing to various reasons such as enhancing its affinity to a target, raising its stability, and making its synthesizing easier.

Any substituent group may be a specific substituent group according to the present invention, as long as it is contained in the functional substance, and the amplification of the functional substance can proceed when the substituent group is eliminated from the substance. A modifying group when a functional substance contains a modified nucleotide sequence with the modifying group, is an example. This modifying group is not necessarily contained in all the nucleotide units of the nucleotide sequence. It is enough if it is included in part of them.

Such a specific substituent group typically refers to one for which the amplification does not proceed when its substituent group is present, and the amplification proceeds when its substituent group is absent. However, one for which the amplification proceeds even when its substituent group is present, may also be acceptable. This is because the purpose of the present invention to analyze the structure of the specific substance can be achieved, if the specific substituent group is eliminated to allow the amplification to proceed, whether it hinders the amplification or not. It is to be noted that although there are occasions in which as a result of elimination of a specific substituent group, a different type of substituent group is introduced to the place where the specific substituent group was present, such replacement by a different type of substituent group is acceptable, as long as the amplification can proceed.

There is no particular limitation to such a specific substituent group, and any group may be appropriately chosen, depending on purposes. Natural or non-natural amino acid groups, metal complex groups, fluorescent pigment groups, oxidation/reduction pigment groups, groups which can be spin-labeled, alkyl groups with a carbon number from 1 to 10, and groups represented by formulae (1) to (10), are examples. Each of the groups may further have a substituent group. They may be used singly, or a plurality of them may be used together.

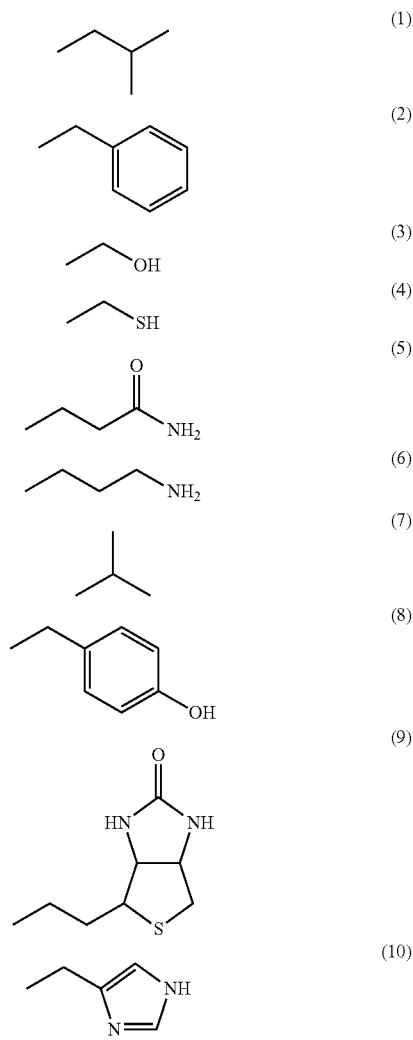

There is no particular limitation to the above-described natural or non-natural amino acid groups, and any natural or non-natural amino acid group may be appropriately chosen, depending on purposes. Groups derived from valine, leucin, isoleucine, alanine, alginine, glutamine, lysin, aspartic acid, glutaminic acid, proline, cysteine, threonine, methionine, histidine, phenylalanine, tylosin, tryptophan, asparagine, glycine, serine, etc., are examples.

There is no particular limitation to the above-described metal complex groups, as long as they are derived from coordination compounds of metal ions with ligands, and any metal complex group may be appropriately chosen, depending on purposes. Groups derived from Ru bipyridyl complexes, ferrocene complexes, nickel imidazole complexes, etc. are examples.

There is no particular limitation to the above-described fluorescent pigment groups, and any fluorescent pigment group may be appropriately chosen, depending on purposes. Groups derived from fluorescent pigments of the fluorescein family, rhodamine family, eosin family, and NBD family, are examples.

There is no particular limitation to the above-described oxidation/reduction pigment groups, and any oxidation/reduction pigment group may be appropriately chosen, depending on purposes. Groups derived from leuco pigments such as leucoaniline and leucoanthocyanin, are examples.

There is no particular limitation to the above-described groups which can be spin-labeled, and any group which can be spin-labeled may be appropriately chosen, depending on purposes. Groups derived from iron N-(dithiocarboxy)sarcosine, TEMPO (tetramethylpiperidine) derivatives, etc., are examples.

There is no particular limitation to the above-described alkyl groups with a carbon number from 1 to 10, and any alkyl group with a carbon number from 1 to 10 may be appropriately chosen, depending on purposes. Methyl group, ethyl group, propyl group, isopropyl group, butyl group, isobutyl group, tert-butyl group, pentyl group, neopentyl group, hexyl group, cyclohexyl group, octyl group, nonyl group, decyl group, etc. are examples.

In addition, in this specificattion, when a DNA sequence or an RNA sequence is used as a functional substance or its candidate, substituent groups (protective groups) are often introduced for the purposes including prevention of side reactions during the synthesis or provision of their solubility into organic solvents. The protective groups and the specific substituent groups according to the present invention may be the same groups or different from each other. Either of them may constitute part of the other.

(Candidates for a Functional Substance)

There is no particular limitation to the candidates for a functional substance according to the present invention, and any substances may be chosen. One example is a group of substances that are synthesized from a raw material composition from which a functional substance for a certain purpose may be synthesized. In this case, if a substance that has a specific substituent group is used as one component of the raw material, a group of substances that have the specific substituent group can be obtained. There is no particular limitation to the number of the candidates for a functional substance. There may be a case in which only one functional substance is selected from among thousands to tens of thousands of candidates for the functional substance.

There is no particular limitation to the method for synthesizing the candidates, and any method may be appropriately chosen, depending on purposes. When modified nucleotides are used, methods in which oligomers including dimers and/or trimers are synthesized by a diester method, triester method, phosphite method, phosphoramidite method, H-phosphonate method, thiophosphite method, or the like, followed by polymerizagtion, are enumerated as the examples. Among them, the phosphoramidite method is desirable.

In the above-describe phosphoramidite method, in general, the key reaction is a condensation reaction between a nucleoside phosphoramidite and a nucleoside in the presence of tetrazole as an accelerator. While this reaction usually occurs both with the hydroxy group of the sugar group and the amino group of the nucleoside base group in a competitive manner, it is necessary to make the reaction selectively occur only with the hydroxy group of the sugar group in order to synthesize a desired nucleotide. Accordingly, modification with a protective group is carried out to prevent side reactions with the amino group.

There is no particular limitation to the method for polymerizing the above-described oligomers, and any method may be appropriately chosen from known methods, depending on purposes. For example, a method in which a DNA synthesizer (automatic DNA synthesizer) is used, and a method in which monomer blocks are arranged onto random oligonucleotide sequences that have been produced beforehand, and they are subjected to annealing for the bonding to occur by the action of a DNA ligase or RNA ligase, are preferable examples.

There is no particular limitation to the method for using the above-described DNA synthesizer (automatic DNA synthesizer), and any method may be appropriately chosen, depending on purposes. For example, a method in which a DNA synthesizer (automatic DNA synthesizer) such as shown in FIG. 1 is used, reagents obtained by mixing plural types of modified nucleotide dimers that have been synthesized are used, and candidates for a functional substance that comprise modified nucleotide sequences with all possible and random sequencings, are produced by polymerizing the reagents taken up by suction through nozzles 7 according to the control of a controller, or the like is preferable. This method is advantageous, since it is possible to produce candidates for a functional substance efficiently.

(Selection)

There is no particular limitation to the selection according to the present invention, and any method may be appropriately chosen, depending on purposes. In the case of a functional substance comprising a modified nucleotide sequence, various methods including affinity chromatography, filter combination, liquid-liquid separation, filtration, gel shift, and density gradient centrifuging, are enumerated as the examples. They may be used singly or two or more of them may be used in combination. Among them, the affinity chromatography is preferable. One type of functional substance may be selected. Plural types of functional substances may also be selected.

The affinity chromatography is a separation/purification means utilizing the biological affinity with which specific components are liable to be bound together. To be concrete, when a functional substance comprises a modified nucleotide sequence, a target is fixed on a column filler made of a resin or the like, equilibrium is achieved by addition of a binding buffer fluid, a solution comprising candidates for the functional substance is then introduced into the column, then, the column is kept standing under a certain condition to make modified nucleotide sequences that have an affinity to the target adsorbed onto the column, and components other than the remaining modified nucleotide sequences can be removed by fully washing it with a binding buffer fluid. Afterwards, a functional substance or functional substances comprising the above-described modified nucleotide sequences are recovered and selected by introducing a solution containing the target or pure water into the column.

When there are two or more targets that are unknown themselves (for example, in the case of an internal organ or serum), functional substances bound with the targets may be selected by partitioning and fixing, for mapping, the targets on a matrix having one of one-dimensional to three-dimensional spatial arrangements, and making candidates for functional substances act on the matrix on which the targets are fixed and partitioned.

There is no particular limitation to the method for fixing a target on a matrix, and any method may be appropriately chosen, depending on purposes. When the target is a protein, for example, a western blot method in which a target is subjected to a polyacrylamide electrophoresis (for example, SDS-PAGE or the like) treatment, followed by transferring it to a matrix in a film form, a dot blot method in which a target or a target diluted in a solution is directly seeped into a matrix in a film form, a slot blot method, etc. are enumerated. Among them, the western blot method is preferable, since even a tiny amount of protein contained in a solution of a complicate composition such as a fluid extracted from cells is clearly detectable. The western blot method is a method to detect a specific protein or proteins in a protein mixture, by combining an excellent separating ability of electrophoresis and a high specificity of antigen-antibody reactions. It is a method in which samples are subjected to SDS-PAGE, electrofocusing method, two-dimensional electrophoresis, or the like, followed by electrically transferring the proteins from a gel to a film matrix for fixing. There is no particular limitation to the film matrix, and any film matrix may be appropriately chosen, depending on purposes. A nitrocellulose film that has a high hydrophobic property and is easily bound with proteins, a PVDF (polyvinylidene difluoride) film that is excellent in its hydrophobic property, etc. are preferable examples.

Preliminary purification operation may be added to separate the synthesized candidates for a functional substance from other substances prior to the above-described selection step. Techniques similar to those for the above-described selection may be applied under conditions that the affinity is exhibited to a functional substance that has an affinity to the target and the candidates for the functional substance, but is not exhibited to the other substances.

In addition, purification of the functional substance may be carried out in the course of the above-describe selection step. The purification is preferably carried out by liberating the functional substance from the target while monitoring the dissociation constant between the target and the functional substance. This method is advantageous, since a functional substance having a desired dissociation constant is selected efficiently by a minimum treatment cycle of one. Hereupon, the dissociation constant may be set arbitrarily, depending on the target. The dissociation constant may be measured with a measuring apparatus utilizing surface plasmon resonance, for example.

It is to be noted that it is also possible, in the selection step, to regenerate the support, for example, by utilizing an interactive action between two or more substances having different dissociation constants, selecting a functional substance through a washing operation that is suitable for a small dissociation constant, and then carrying out a washing operation that is suitable for a large dissociation constant. Even though there are two or more targets, it is still also possible to regenerate the support, and collectively select plural different functional substances with one support, efficiently.

(Amplification)

The amplification according to the present invention may be any method, as long as it can amplify a functional substance after the elimination of a specific group, and any method may be appropriately chosen from known methods. When a functional substance comprises a nucleotide sequence, the PCR method, the LCR (Ligase Chain Reaction) method, the 3SR (Self-Sustained Sequence Replication) method, the SDA (Strand Displacement Amplification) method, the RT-PCR method, the ICAN method, the LAMP method, etc., are enumerated as the examples. They may be singly applied, or two or more of them may be applied. Among them, the PCR method is preferable.

Here, the PCR method is briefly explained. The PCR method is a method in which a specific oligonucleotide region can be amplified by several hundreds of thousands times, by repeating an in vitro DNR synthesizing reaction with a DNA-replicating enzyme. In the PCR method, the extension reaction of the used primer is carried out by introducing four nucleotide triphosphates (deoxyadenosine triphosphate, deoxyguanosine triphosphate, deoxycytidine triphosphate, and thymidine triphosphate or deoxyuridine triphosphate; a mixture thereof being sometimes called dNTP) into a primer as a base substance.

As a DNA-replicating enzyme for carrying out the extension reaction, any arbitrary DNA polymerase such as *E. coli* DNA polymerase I, a Klenow fragment of *E. coli* DNA polymerase I, and T4 DNA polymerase, Taq DNA polymerase, Tth DNA polymerase, Vent DNA polymerase, etc. are enumerated.

(Determination of the Structure of a Functional Substance)

There is no particular limitation to the method for determining the structure of a functional substance according to the present invention, and any known method may be employed. The "determination of the structure" in the structure determination of a functional substance according to the present invention may include determination of any structure such as the order of sequence of atoms. When the functional substance comprises a nucleotide sequence, it typically means to determine the nucleotide sequencing.

For the determination of the nucleotide sequences, DNA sequencers (automatic DNA base sequence determining apparatus) or the like using a method by means of gene cloning, a chain terminator method, the Sanger method, a dideoxy method, or the like, may be utilized. They may be singly applied, or two or more of them may be applied.

In the above-described gene cloning, a host cell is genetically transformed by an expression vector into which an amplified nucleotide sequence is integrated, and the genetically transformed host can be produced through propagating by culture or the like. As the above-described expression vector, a plasmid vector, a bacteriophage vector, a chimera vector of a plasmid and a bacteriophage are enumerated. As the above-described host cell, a prokaryotic cell such as *Bacillus coli* and *Bacillus subtilis*, an eukaryotic microorganism such as yeast fungus, animal cells, etc., are enumerated.

(Elimination of a Specific Substituent Group)

There is no particular limitation to the elimination of a specific substituent group according to the present invention, and any known method may be employed. Scission of a cis-diol by means of periodic acid oxidation, scission of a silyl groups by means of a fluorine ion, scission by means of an acid and alkali, scission by means of an enzymatic reaction, and scission by means of an optical reaction are examples.

Figure 2:
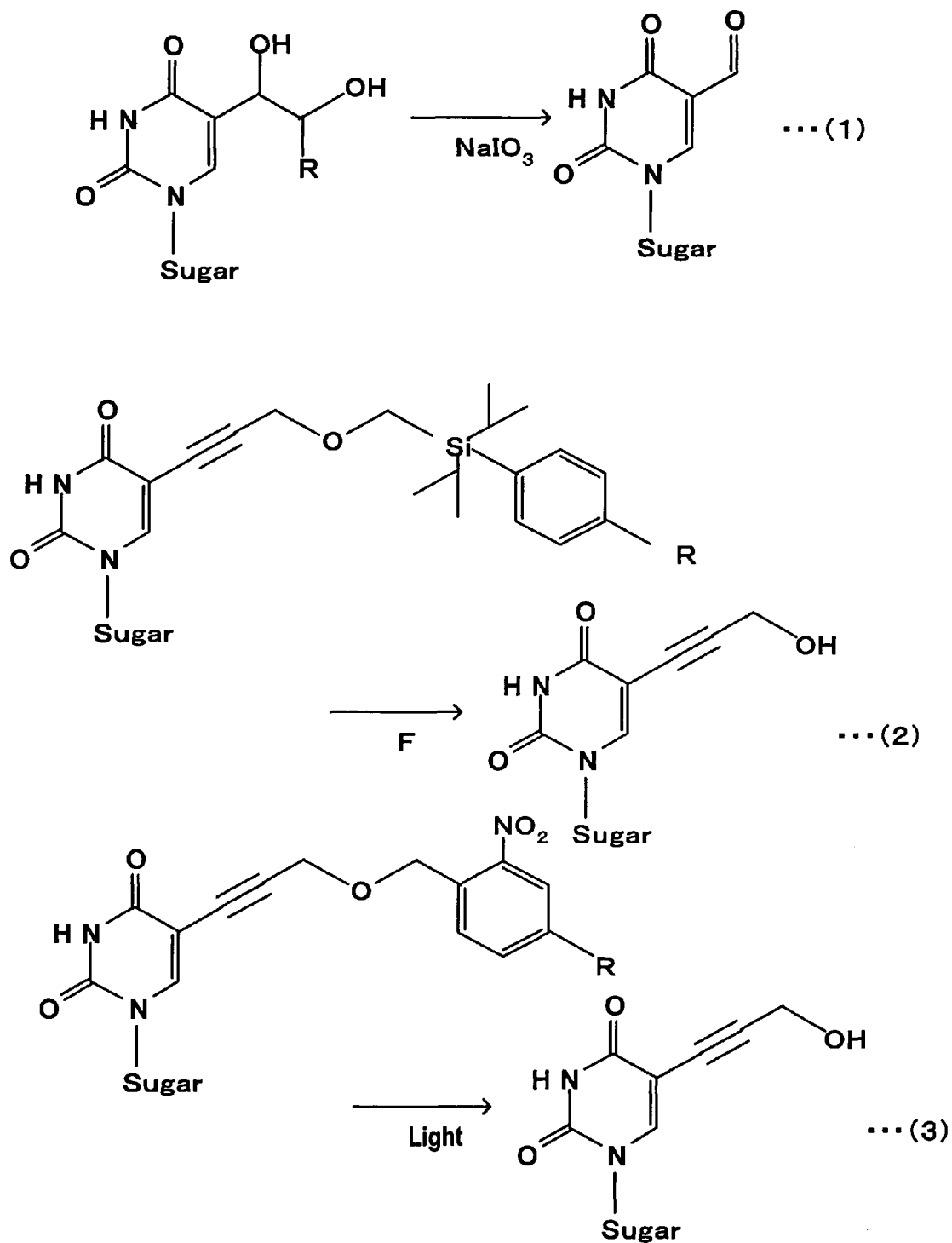
FIG. 2 shows examples of scission of a cis-diol by means of periodic acid oxidation, scission of a silyl group by means of a fluorine ion, and scission by means of an optical reaction.

FIG. 2, (1) shows an example of scission of a cis-diol by means of periodic acid oxidation, (2) shows an example of scission of a silyl group by means of a fluorine ion, and (3) shows an example of scission by means of an optical reaction. In any case, part of the substituent group of deoxy-5-substituted uridine is replaced with OH as a result of the scission.

The "elimination of a specific substituent group" according to the present invention includes cases in which part of a substituent group is replaced, just like the above-described case. In other words, whether the "elimination of a specific substituent group" according to the present invention has occurred or not can be determined by whether the subsequent amplification is possible or not.

It is to be noted that the above-described protective group is also usually subjected to elimination prior to the determination of the structure of a functional substance. Known methods may be employed for the elimination. The elimination of a protective group is often carried out prior to the selection of a functional substance, because it makes it easier to remove substances other than the functional substance. However, the elimination may also be carried out after the selection of a functional substance. Both the eliminations of a protective group and a specific substituent group may be carried out in the same operation.

(Production of a Functional Substance)

By utilizing the above-described method for determining the structure of a functional substance, it is easy to produce this functional substance afterwards. There is no particular limitation to the method that can be used for this production step, and any known method may be employed. In the case of a functional substance comprising a nucleotide sequence, for example, the same method as was explained for the candidates for a functional substance may be utilized. In this case, it is possible to produce the functional substance in a high yield, by choosing raw material compositions.

According to the procedure described above, it is possible by the present invention to easily determine the structure of a functional substance that has a high affinity to a target, and produce it easily. It is possible to apply the present structure determining method and production method even to a functional substance that cannot be amplified as it is.

Furthermore, in many cases, it is possible to select a plurality of functional substances at the same time to determine the structures, or to use a plurality of targets in order to select a plurality of functional substances at the same time and determine the structures. Furthermore, it is often possible to perform the selection and the structure determination even when a target contains foreign substances.

According to the present invention, it is possible, for example, to further develop analysis of the structure of a target (the structure of a sequence of a protein, for example), screening thereof, etc., and apply the obtained results to medicines, drug delivery, biosensors, control of gene expression level, overcoming of diseases due to gene defects, elucidation of functions of proteins translated by genes, development of reactive catalysts, etc.

EXAMPLES

Next, examples of the present invention will be explained in detail.

Example 1

(Example of a Structure Determining Method and Production Method)

Figure 3:
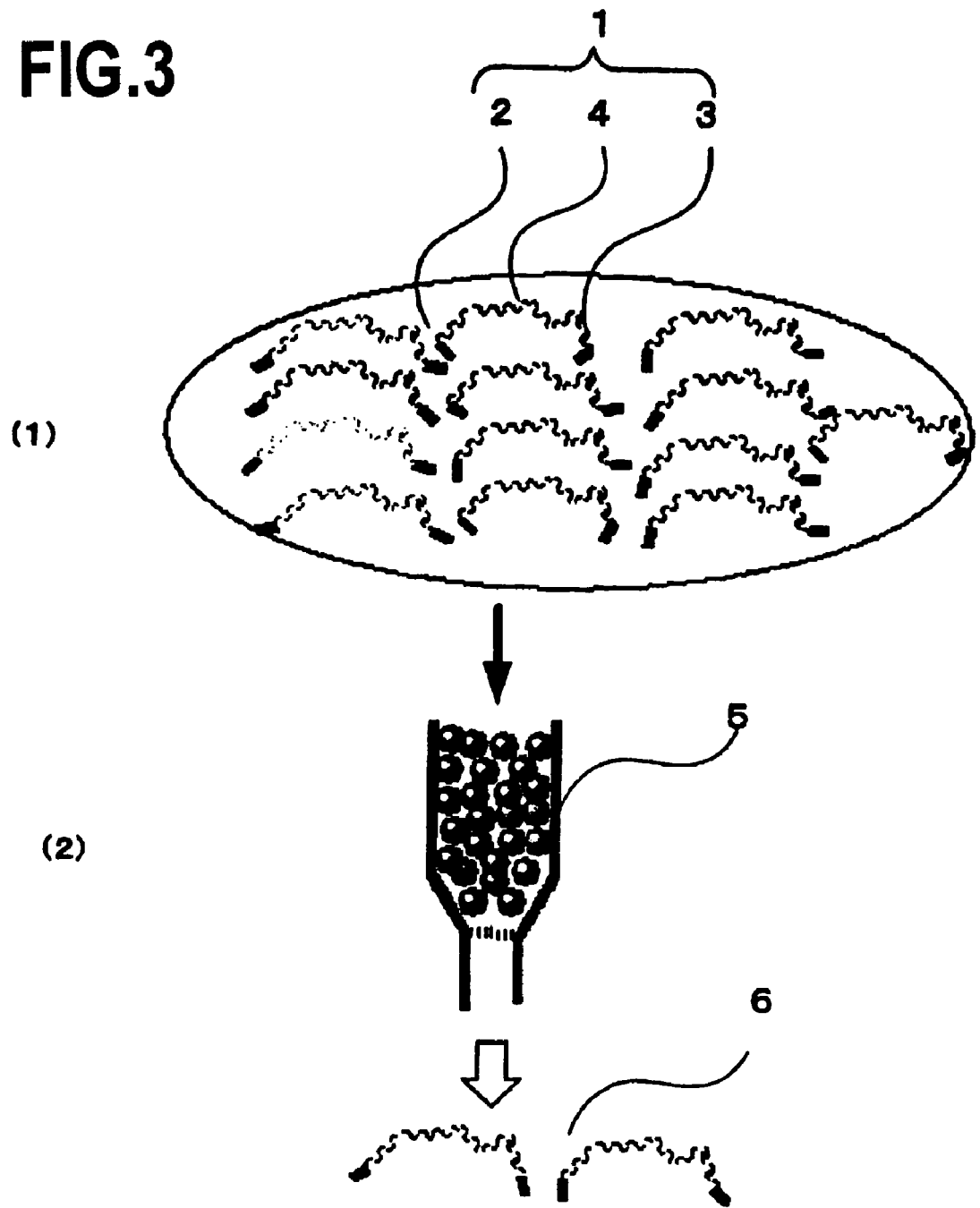
FIG. 3 is a view illustrating a structure determining method and production method according to the present invention.
Figure 4A:
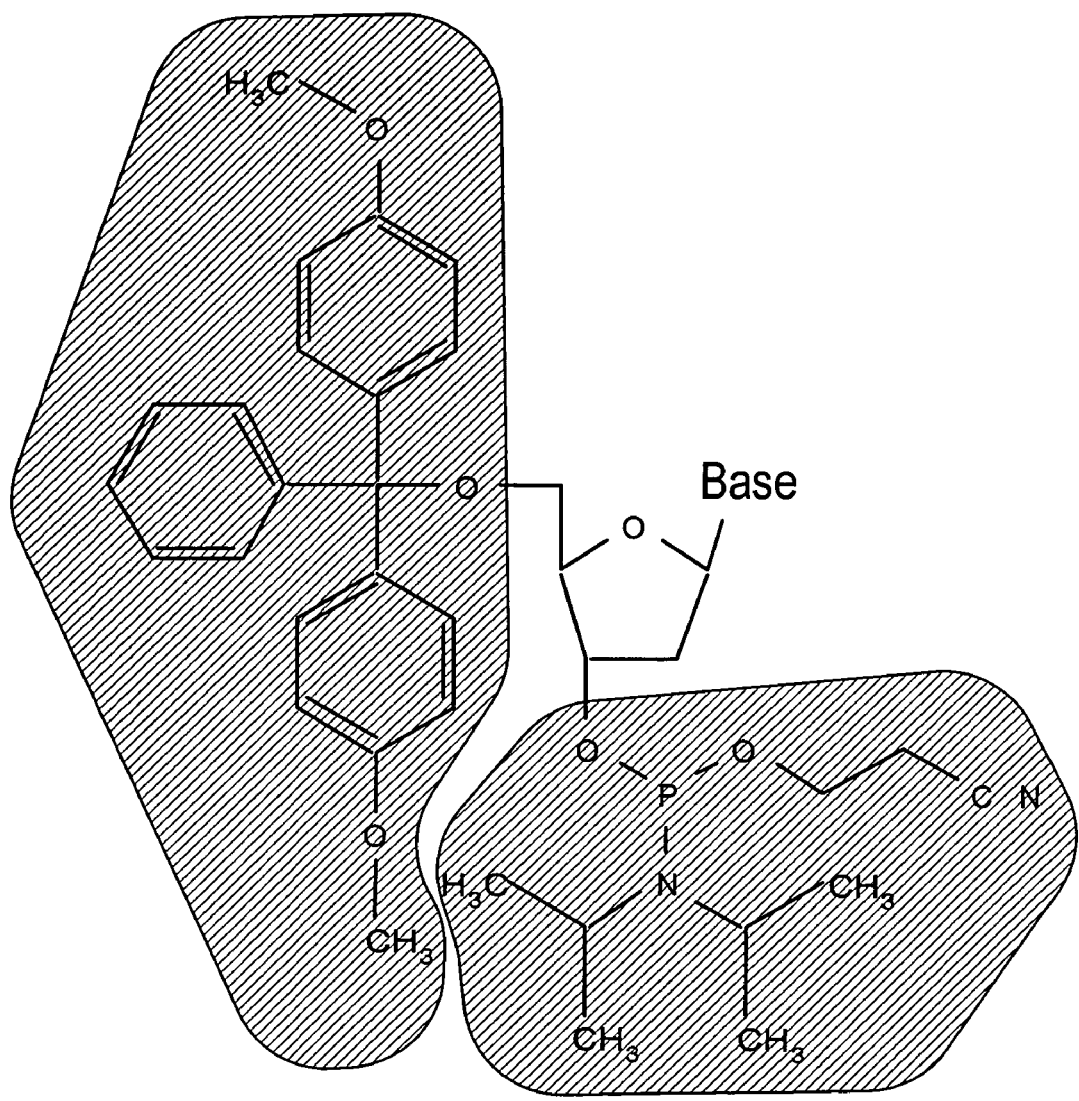
FIG. 4A shows the structure of an amidite.
Figure 4B:
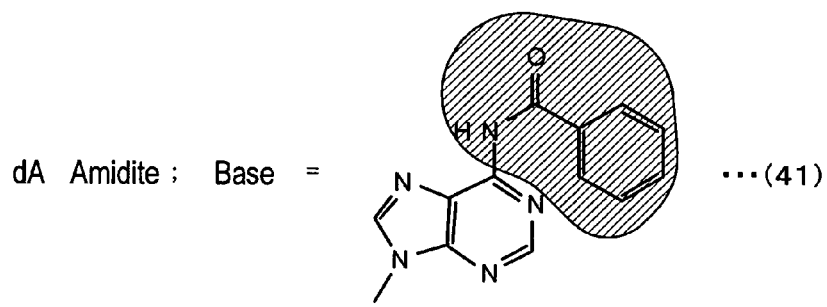
FIG. 4B shows the structures of Bases of dA and dG amidites.
Figure 4B:
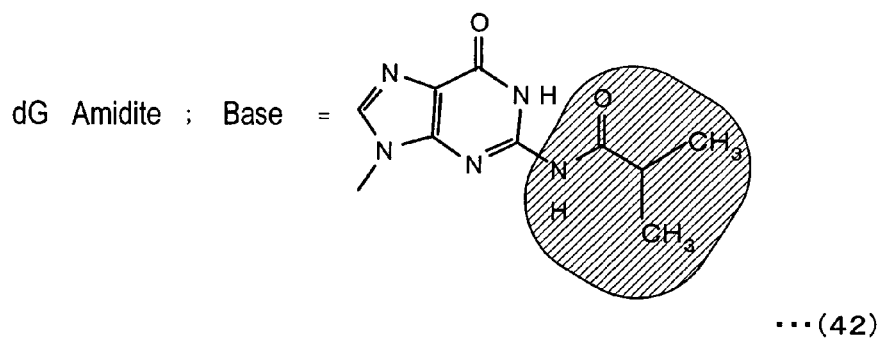
Figure 4C:
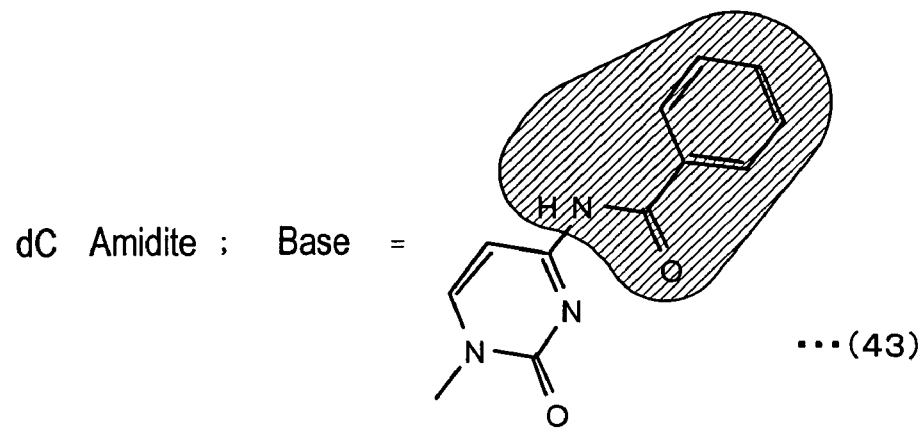
FIG. 4C shows the structure of Bases of dC and dT amidites.
Figure 4C:
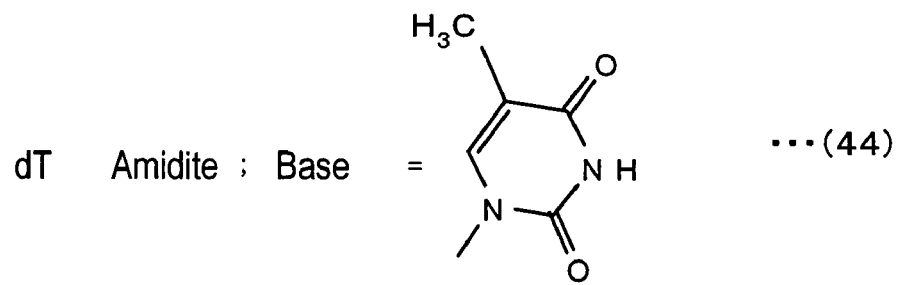
Figure 4D:
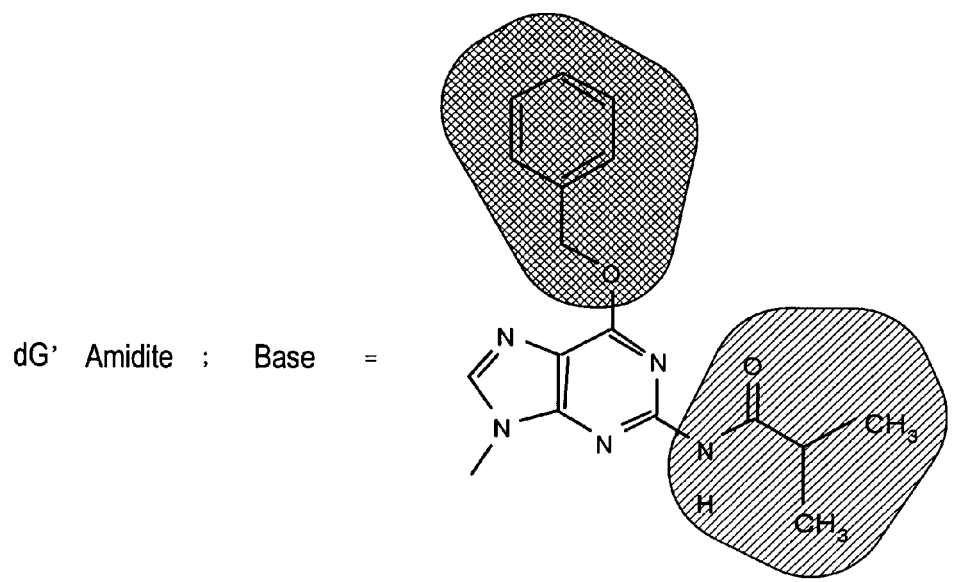
FIG. 4D shows the structure of Bases of dG' and dT' amidites.
Figure 4D:
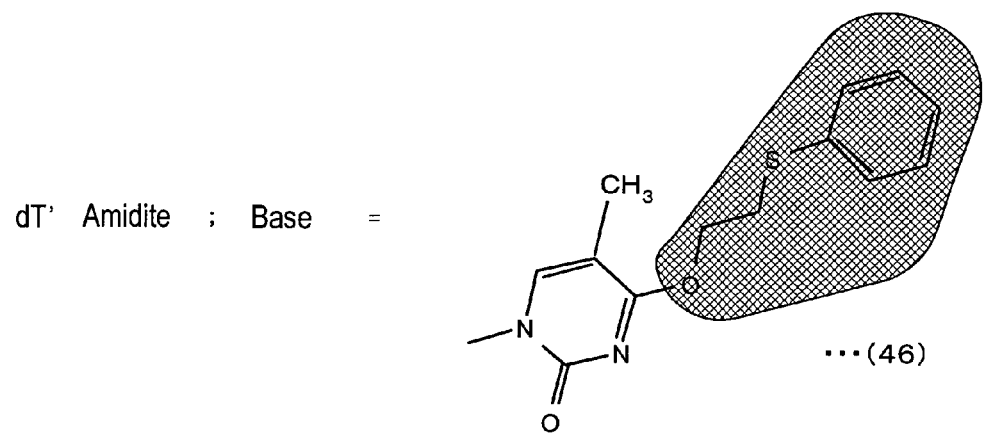

A structure determining method and a production method according to the present invention will be described, using FIG. 3 for the illustration. FIG. 3, (1) is a schematic view showing a group of candidates for a functional substance according to the present invention. Modified nucleotide sequences are used as the candidates for a functional substance.

A modified nucleotide sequence 1 is composed of fixed nucleotide sequence parts 2 and 3, and a modified nucleotide sequence part 4. The base sequences of the fixed nucleotide sequence parts 2 and 3 are known, and the base sequence of the modified nucleotide sequence part 4 is randomized.

This group of candidates for a functional substance is passed through an affinity column 5 supporting a target shown in FIG. 3, (2). By this, a functional substance that has an affinity to the target is caught by the affinity column. Afterwards, a solution containing the target is passed through the affinity column to recover the liberated functional substance 6. The selection according to the present invention is carried out in this way.

Next, the modifying group of the recovered functional substance is eliminated. The reactions illustrated in FIG. 2 are utilized, for example. Afterwards, the functional substance from which the modifying group has been eliminated is amplified so as to determine the structure of the amplified functional substance, and then produce the functional substance.

Example 2

(Amplification in a Case having a Base that is not Recognized by a DNA Amplification Enzyme)

In this example, a DNA sequence, ttatcaacaaaatactccaattgN$_{50}$gaaagatcccaacgaaaag (SEQ ID NO: 1) was synthesized with an automatic DNA synthesizer (Applied 391A).

To be concrete, the part N$_{50}$ (the numeral 50 represents the number of a nucleotide unit) was synthesized by preparing (1) a mixture of dA, dG, dC and dT, (2) a mixture of dA, dG', dC and dT, and (3) a mixture of dA, dG, dC and dT', using amidites, dA, dG, dC, dT, dG' and dT'. Hereafter, the groups of candidates for a functional substance obtained by using these mixtures are referred to as random mixes I, II, and III, respectively.

Here, the structures of amidites, dA, dG, dC, dT, dG', and dT' are shown in FIGS. 4A to 4D. In FIGS. 4A to 4D, dA amidite is one that has structure (41) at the Base position of the amidite in FIG. 4A, dG amidite is one that has structure (42) at the Base position of the amidite in FIG. 4A, dC amidite is one that has structure (43) at the Base position of the amidite in FIG. 4A, dT amidite is one that has structure (44) at the Base position of the amidite in FIG. 4A, dG' amidite is one that has structure (45) at the Base position of the amidite in FIG. 4A, and dT' amidite is one that has structure (46) at the Base position of the amidite in FIG. 4A.

The affinity resin was synthesized from pCAATTGGAGTATTTTGATAA (SEQ ID NO: 2) sequence and TTATCAACAAAATACTCCAATTGAACCACTGCTT (SEQ ID NO: 3) sequence, using a DNA ligase and using an SNP (Single Nucleotide Polymorphism) analyzing apparatus, SNPsi from GL Science. This affinity resin was used for carrying out preliminary purification of random mixes I to III, by separating DNA sequences (candidates for a functional substance according to the present invention) that can be bound with the above-described sequences from the other substances. Afterwards, it was washed with a binding buffer fluid having a composition of 10 nM Tris-HCl, pH=7.4, 0.3 M of NaCl.

Then, the protective groups were eliminated from each of the above-described random mixes I, II and III, with a concentrated ammonia solution at 55° C. After the elimination treatment for 8 hours, the random mixes were passed through the affinity resin. The protective groups to be eliminated in this example are shown as hatched areas in FIGS. 4A to 4D.

Then, DNA sequences removed from the affinity resin by increasing the temperature were recovered. The concentration of each DNA sequence of random mixes I, II and III was determined with a UV absorption intensity meter.

It is to be noted that while in the present invention, the selection is then carried out, using an affinity resin for selectively sorting out only a specific functional substance, it is omitted in this example to simplify the explanation.

Next, the amount of the above-described DNA molecules was adjusted to be 1×10$^4$ molecules in one reaction pot (20 μL), and a PCR was carried out using dynamo QPCRKIT, and 0.3 μM of TTATCAACAAAATACTCCAATTG (SEQ ID NO: 4) sequence and 0.3 μM of CTTTTCGTTGGGATCTTTC (SEQ ID NO: 5) sequence as primers. The conditions for one cycle were 95° C.×10 seconds, 57.5° C.×20 seconds, and 72° C.×60 seconds. As a result, increase of fluorescence was observed at about 30th cycle, only from the liquid recovered from random mix I for which an amidite under the standard condition was used. This fluorescent light was derived from SYBR-GREEN I included in the dynamo QPCRKIT.

This result shows that a functional substance that could be amplified was obtained only from the liquid recovered from random mix I. That is, amplification was hindered, regarding random mixes II and III.

Next, elimination of the modifying group (substituent group according to the present invention) from the liquid recovered from random mix II, was carried out, using Human O6-alkylguanine-DNA alkyltransferase (hAGT). As a result of a PCR carried out onto the product thereof according to the above-described conditions, increase of fluorescence was observed at about 30th cycle. The substituent group eliminated at the time is shown as a crosshatched area in formula (45) in FIG. 4D.

Furthermore, random mix III was oxidized, using m-chloroperbenzoic acid, and the substituent group was then eliminated with a concentrated ammonia solution. As a result of a PCR carried out onto the thus obtained product according to the above-described conditions, increase of fluorescence was observed at about 30th cycle.

These results show that while it was not possible to amplify the functional substances from the liquids recovered from random mixes II and III, it was possible to amplify them by eliminating the modifying group.

Example 3

(Elimination of a Substituent Group)

DNA sequences having a sequencing of DACGT"T was synthesized, using dA, dC, dG, dT and dT" amidites. A part of the product was decomposed to monomers with a phosphodiesterase+an alkali phosphatase, and the monomers were compared with a standard sample in an HPLC analysis. As a result, it was found that no amino group was generated, and the protective group was not eliminated.

The DNA sequence was oxidized with m-chloroperbenzoic acid, then the substituent group (acting also as a protective group in this case) was eliminated with a concentrated ammonia solution, and the product was decomposed to monomers with a phosphodiesterase+an alkali phosphatase. As a result, it was confirmed that dA, dC, dG, 5-propagylamino dU, and dT were produced in an HPLC analysis.

Figure 5:
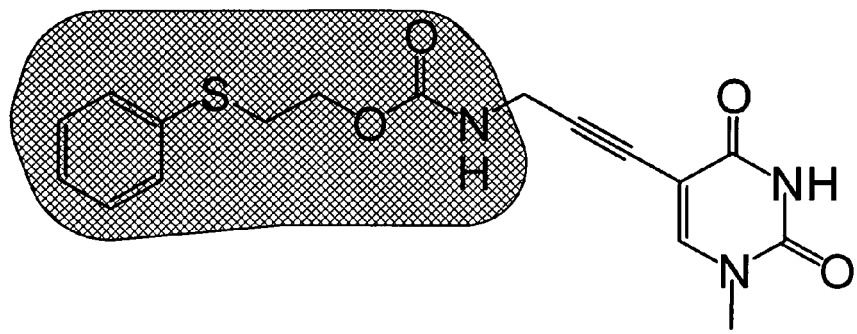
FIG. 5 shows the structure of Base of dT"
Figure 6:
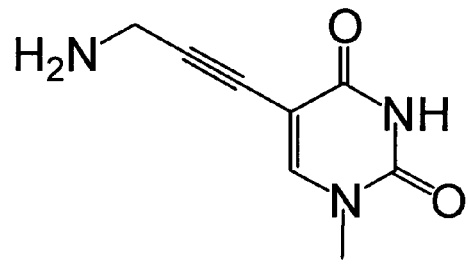
FIG. 6 shows the structure of Base of 5-propagylamino dU.

FIG. 5 shows the Base structure of dT". In FIG. 5, the substituent group according to the present invention is shown as a crosshatched area. FIG. 6 shows the Base structure of 5-propagilamono dU.

Examples 4

(Confirmation of the Tolerance of a DNA with its Substituent Group Eliminated to the DNA Polymerase)

Using dT''' amidite generated from 5-propagylamino dU with the dT'' substituent eliminated under the usual protection conditions (concentrated ammonia solution, at 55° C. for 8 hours), ttatcaacaaaatactccaattggcgatggccctgtccdT'''dT'''adT'''accaga-caaccattacctgtccacacaatctgcccttcgaaagatcccaacgaaaag (SEQ ID NO: 6) sequence was synthesized with an automatic DNA synthesizer.

After eliminating the protective group with an concentrated ammonia solution at 55° C. in 8 hours, the product was purified (that is, selected) by gel electrophoresis. It was confirmed separately by preparing oligomers similar to dT'', that elimination of the protective group occurs under these conditions.

It is to be noted that the protective group in this case has also a role of a substituent group according to the present invention. Therefore, separate elimination of the substituent group was not carried out.

As a result of amplification in the same way as EXAMPLE 1, using this DNA sequence with its protective group eliminated, increase of fluorescence was observed at about 30th cycle. Furthermore, as a result of determination of the sequence of a PCR product, it was found that A was chosen as a complementary base of the base obtained by eliminating the modifying group from dT'''. That is, it was confirmed that the DNA sequence obtained by eliminating the modifying group from dT''' could be amplified by a PCR.

Figure 7:
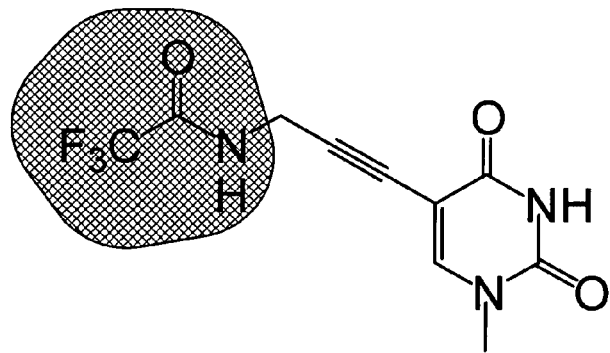
FIG. 7 shows the structure of Base of dT'"

FIG. 7 shows the Base structure of dT'''. In FIG. 7, the substituent group according to the present invention is shown as a crosshatched area.

Examples 5

(Elimination of a Substituent Group)

Figure 8:
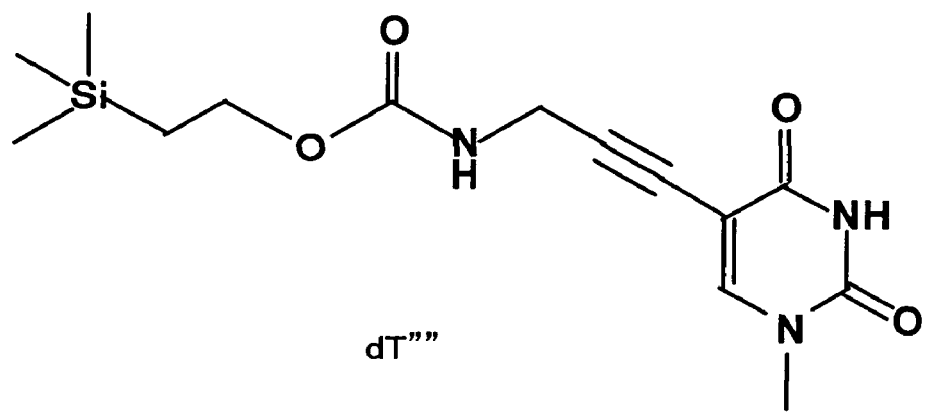
FIG. 8 shows the structure of Base of dT""

DNA sequences having a sequencing of DACGT""T was synthesized, using dA, dC, dG, dT and dT"" amidites. A part of the product was decomposed to monomers with a phosphodiesterase+an alkali phosphatase, and the monomers were compared with a standard sample in an HPLC analysis. As a result, it was found that no amino group was generated, and the substituent group according to the present invention was not eliminated. FIG. 8 shows the Base structure of dT"".

The substituent group was eliminated by subjecting the DNA sequences to a t-Bu₄NF treatment, and the product was decomposed to monomers with a phosphodiesterase+an alkali phosphatase. As a result, it was confirmed that dA, dC, dG, 5-propagylamino dU, and dT were produced in an HPLC analysis.

Examples 6

(Elimination of a Substituent Group)

Figure 9:
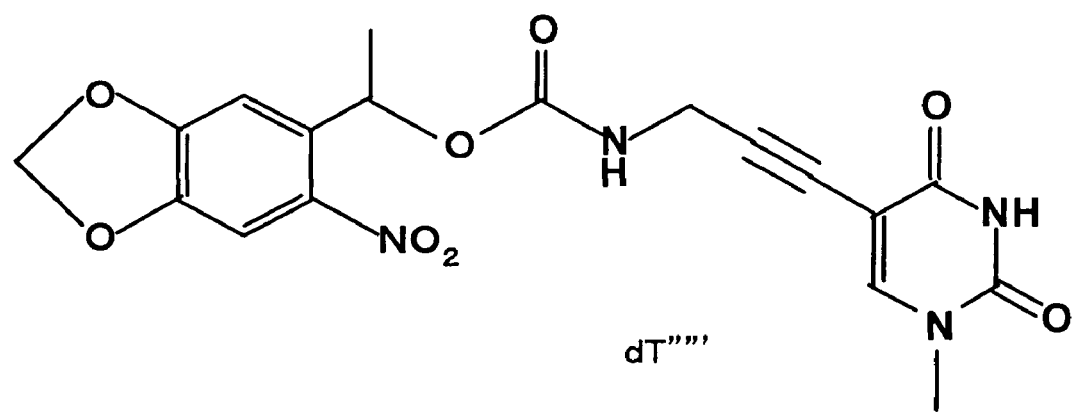
FIG. 9 shows the structure of Base of dT""'.

DNA sequences having a sequencing of dACGT"""T was synthesized, using dA, dC, dG, dT and dT"""amidites. A part of the product was decomposed to monomers with a phosphodiesterase+an alkali phosphatase, and the monomers were compared with a standard sample in an HPLC analysis. As a result, it was found that no amino group was generated, and the substituent group according to the present invention was not eliminated. FIG. 9 shows the Base structure of dT""".

The substituent group was eliminated by subjecting the DNA sequences to irradiation with a 365-nm light, and the product was decomposed to monomers with a phosphodiesterase+an alkali phosphatase. As a result, it was confirmed that dA, dC, dG, 5-propagylamino dU, and dT were produced in an HPLC analysis.

What is claimed is:

1. A method for determining the structure of a functional substance, which is a substance having an affinity to a target, comprising:

synthesizing functional substance candidates having a specific substituent group which bonds covalently thereto, and hinders a reaction selected from the group consisting of PCR, LCR, Self-Sustained Sequence Replication, SDA, RT-PCR, ICAN, and LAMP;

selecting and separating a functional substance having a specific substituent group which bonds covalently thereto, hinders said reaction, and has an affinity to the target from among said functional substance candidates having the specific substituent group;

eliminating the specific substituent group from said selected functional substance having the specific substituent group, to produce a substance without the specific substituent group;

amplifying said substance without the specific substituent group by said reaction, to produce an amplified substance; and determining the structure of said amplified substance as the structure of said selected functional substance, wherein said functional substance is a nucleotide sequence; and said specific substituent group comprises at least one group selected from the groups represented by formulae (1) to (10)

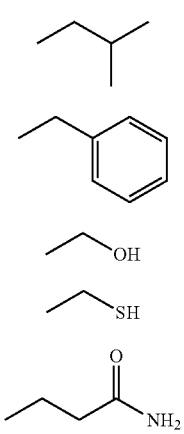

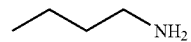

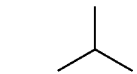

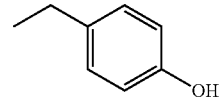

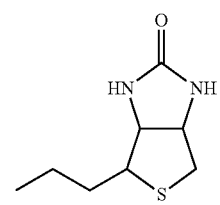

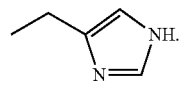

2. A method for determining the structure of a functional substance according to claim 1, wherein said specific substituent group is eliminated from the functional substance, by scission of a cis-diol by means of periodic acid oxidation, by scission of a silyl group by means of a fluorine ion, by scission by means of an acid and alkali, by scission by means of an enzymatic reaction, or by scission by means of an optical reaction.

3. A method for determining the structure of a functional substance according to claim 1, wherein said functional substance comprises a modified nucleotide sequence.

4. A method for determining the structure of a functional substance according to claim 1, wherein said functional substance is a modified DNA sequence or a modified RNA sequence.

5. A method for determining the structure of a functional substance according to claim 1, wherein said target is at least one substance selected from the group consisting of proteins, lipoproteins, glycoproteins, polypeptides, lipids, polysaccharides, lipopolysaccharides, nucleic acids, environmental hormones, drugs, composite materials thereof, and materials obtained by decomposing these materials.

6. A method for producing a functional substance, which is a substance having an affinity to a target, comprising:

synthesizing functional substance candidates having a specific substituent group which bonds covalently thereto, and hinders a reaction selected from the group consisting of PCR, LCR, Self-Sustained Sequence Replication, SDA, RT-PCR, ICAN, and LAMP;

selecting and separating a functional substance having a specific substituent group which bonds covalently thereto, hinders said reaction, and has an affinity to the target from among said functional substance candidates having the specific substituent group;

eliminating the specific substituent group from said selected functional substance having the specific substituent group, to produce a substance without the specific substituent group;

amplifying said substance without the specific substituent group by said reaction, to produce an amplified substance;

determining the structure of said amplified substance as the structure of said selected functional substance; and producing the functional substance having the specific substituent group, based on said structure of said amplified substance, wherein said functional substance is a nucleotide sequence; and said specific substituent group comprises at least one group selected from the groups represented by formulae (1) to (10)

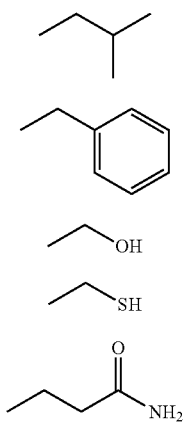

(1)
(2)
(3)
(4)
(5)

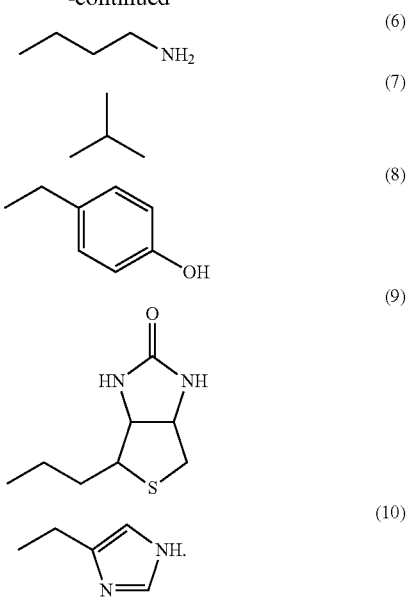

(6)
(7)
(8)
(9)
(10)

7. A method for producing a functional substance according to claim 6, wherein said specific substituent group is eliminated from the functional substance, by scission of a cis-diol by means of periodic acid oxidation, by scission of a silyl group by means of a fluorine ions, by scission by means of an acid and alkali, by scission by means of an enzymatic reaction, or by scission by means of an optical reaction.

8. A method for producing a functional substance according to claim 6, wherein said functional substance comprises a modified nucleotide sequence.

9. A method for producing a functional substance according to claim 6, wherein said functional substance is a modified DNA sequence or a modified RNA sequence.

10. A method for producing a functional substance according to claim 6, wherein said target is at least one substance selected from the group consisting of proteins, lipoproteins, glycoproteins, polypeptides, lipids, polysaccharides, lipopolysaccharides, nucleic acids, environmental hormones, drugs, composite materials thereof, and materials obtained by decomposing these materials.

* * * * *

SEQUENCE LISTING

<160> NUMBER OF SEQ ID NOS: 6

<210> SEQ ID NO 1
<211> LENGTH: 92
<212> TYPE: DNA
<213> ORGANISM: artificial sequence
<220> FEATURE:
<223> OTHER INFORMATION: synthesized sequence
<220> FEATURE:
<221> NAME/KEY: misc_feature
<222> LOCATION: (24)..(73)
<223> OTHER INFORMATION: n is a, c, g, or t

<400> SEQUENCE: 1
ttatcaacaa aatactccaa ttgnnnnnnn nnnnnnnnnn nnnnnnnnnn nnnnnnnnnn    60
nnnnnnnnnn nnngaaagat cccaacgaaa ag    92

<210> SEQ ID NO 2
<211> LENGTH: 23
<212> TYPE: DNA
<213> ORGANISM: Artificial sequence
<220> FEATURE:
<223> OTHER INFORMATION: primer

<400> SEQUENCE: 2
caattggagt attttgttga taa    23

<210> SEQ ID NO 3
<211> LENGTH: 34
<212> TYPE: DNA
<213> ORGANISM: artificial sequence
<220> FEATURE:
<223> OTHER INFORMATION: primer

<400> SEQUENCE: 3
ttatcaacaa aatactccaa ttgaaccact gctt    34

<210> SEQ ID NO 4
<211> LENGTH: 23
<212> TYPE: DNA
<213> ORGANISM: artificial sequence
<220> FEATURE:
<223> OTHER INFORMATION: primer

<400> SEQUENCE: 4
ttatcaacaa aatactccaa ttg    23

<210> SEQ ID NO 5
<211> LENGTH: 19
<212> TYPE: DNA
<213> ORGANISM: artificial sequence
<220> FEATURE:
<223> OTHER INFORMATION: primer

<400> SEQUENCE: 5
cttttcgttg ggatctttc    19

<210> SEQ ID NO 6
<211> LENGTH: 100
<212> TYPE: DNA
<213> ORGANISM: artificial sequence
<220> FEATURE:
<223> OTHER INFORMATION: synthesized sequence
<220> FEATURE:
<221> NAME/KEY: modified_base
<222> LOCATION: (39)..(40)

```
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: modified_base
<222> LOCATION: (42)..(42)
<220> FEATURE:
<221> NAME/KEY: misc_feature
<222> LOCATION: (42)..(42)
<223> OTHER INFORMATION: n is a, c, g, or t

<400> SEQUENCE: 6
ttatcaacaa aatactccaa ttggcgatgg ccctgtccnn anaccagaca accattacct      60
gtccacacaa tctgcccttt cgaaagatcc caacgaaaag                          100
```